US012687502B2

(12) United States Patent
Chen et al.

(10) Patent No.: US 12,687,502 B2
(45) Date of Patent: Jul. 21, 2026

(54) METHOD FOR DETECTING DIAPER WETNESS BASED ON RADIO SIGNAL TECHNOLOGY

(71) Applicant: ZHEJIANG UNIVERSITY, Hangzhou (CN)

(72) Inventors: Yanjiao Chen, Hangzhou (CN); Wenyuan Xu, Hangzhou (CN); Jiangyi Deng, Hangzhou (CN); Meng Xue, Hangzhou (CN); Yijie Bai, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 394 days.

(21) Appl. No.: 18/278,412

(22) PCT Filed: Nov. 21, 2022

(86) PCT No.: PCT/CN2022/133189
§ 371 (c)(1),
(2) Date: Aug. 23, 2023

(87) PCT Pub. No.: WO2024/021379
PCT Pub. Date: Feb. 1, 2024

(65) Prior Publication Data
US 2025/0012738 A1     Jan. 9, 2025

(30) Foreign Application Priority Data
Jul. 29, 2022    (CN) .......................... 202210904762.9

(51) Int. Cl.
    *G01N 22/04*       (2006.01)
    *A61B 5/00*       (2006.01)
         (Continued)

(52) U.S. Cl.
CPC ........... *G01N 22/04* (2013.01); *A61B 5/7235* (2013.01); *G01S 13/34* (2013.01); *G16H 40/67* (2018.01)

(58) Field of Classification Search
None
See application file for complete search history.

(56) References Cited

U.S. PATENT DOCUMENTS

2019/0053707 A1*   2/2019   Lane ...................... G16H 40/67

FOREIGN PATENT DOCUMENTS

CN       110361071 A     10/2019
CN       111461269 A      7/2020
                   (Continued)

OTHER PUBLICATIONS

Daubechies, "Synchrosqueezed wavelet transforms: An empirical mode decomposition-like tool," 2011, Applied and Computational Harmonic Analysis, vol. 30, pp. 243-261 (Year: 2011).*
                   (Continued)

*Primary Examiner* — Ivan R Goldberg
(74) *Attorney, Agent, or Firm* — Bayramoglu Law Offices LLC

(57)            ABSTRACT

A method for detecting diaper wetness based on a ratio signal technology comprises: sending a frequency-modulated continuous wave signal to a diaper through a radar device to obtain a transmission signal $S_T(t)$ and a return signal $S_R(t)$; detecting a static environment factor and a dynamic environment factor, and obtaining continuous radar snapshots; eliminating interference of environmental factors by using a filtering template based on the continuous radar snapshots and object respiration; obtaining an outline of the diaper by using wavelet synchronous compression transformation, and dividing into a training sample set and a testing sample set; and inputting the training sample set and the test (Continued)

Sending a frequency-modulated continuous wave signal to a diaper through a radar device to obtain a transmission signal and a return signal of the radar device Detecting a static environment factor and a dynamic environment factor, and obtaining continuous radar snapshots Eliminating interference of the static environment factor and the dynamic environment factor by using a filtering template based on the continuous radar snapshot and object respiration Obtaining an outline of the diaper by using wavelet synchronous compression transformation, and dividing into a training sample set and a testing sample set Inputting the training sample set and the test sample set into a heuristic mobility network for training until a loss function is converged, obtaining the trained heuristic mobility network, and obtaining diaper wetness of the test sample set sample set into a heuristic mobility network for training until a loss function is converged, obtaining the trained heuristic mobility network, and obtaining diaper wetness of the test sample set.

5 Claims, 3 Drawing Sheets

(51) Int. Cl.
    *G01S 13/34*         (2006.01)
    *G16H 40/67*      (2018.01)

(56)                References Cited

FOREIGN PATENT DOCUMENTS

| | | | |
|---|---|---|---|
| CN | 114184645 A | 3/2022 | |
| CN | 115187815 A | 10/2022 | |
| WO | 2006119523 A1 | 11/2006 | |
| WO | WO-2016195113 A1 * | 12/2016 | .............. F21V 33/00 |

OTHER PUBLICATIONS

Cui, "Heuristic Domain Adaptation," 2020, 34th Conference on Neural Information Processing Systems, pp. 1-13 (Year: 2020).*
Heo, FPGA Implementation of an Efficient FFT Processor for FMCW Radar Signal Processing, 2021, Sensors, Sep. 2021, vol. 21, No. 19, 6443, pp. 1-16 (Year: 2021).*

* cited by examiner

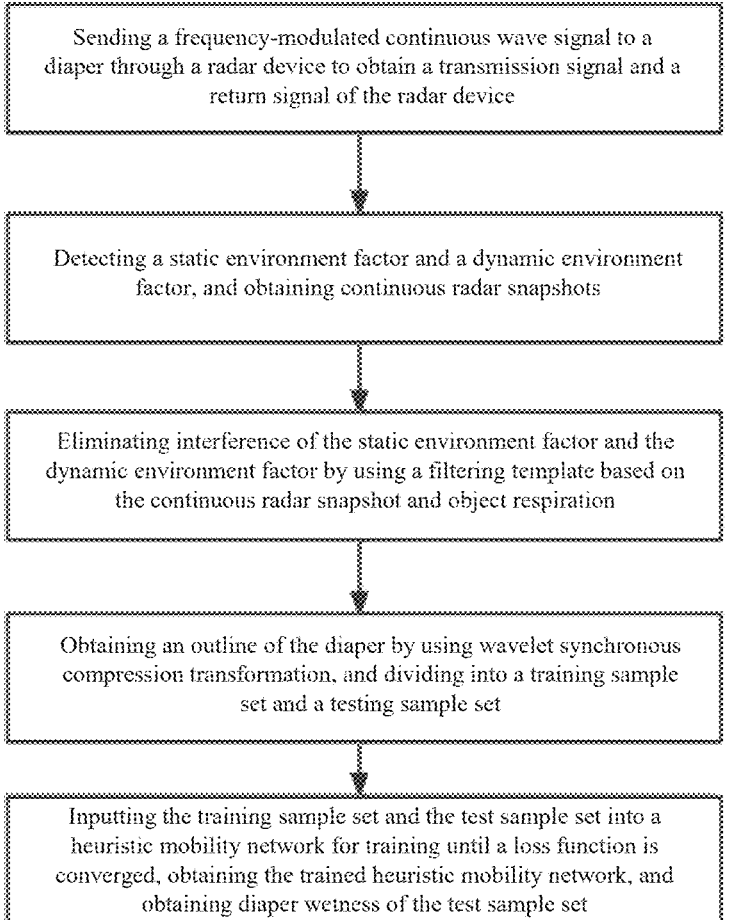

Sending a frequency-modulated continuous wave signal to a diaper through a radar device to obtain a transmission signal and a return signal of the radar device Detecting a static environment factor and a dynamic environment factor, and obtaining continuous radar snapshots Eliminating interference of the static environment factor and the dynamic environment factor by using a filtering template based on the continuous radar snapshot and object respiration Obtaining an outline of the diaper by using wavelet synchronous compression transformation, and dividing into a training sample set and a testing sample set Inputting the training sample set and the test sample set into a heuristic mobility network for training until a loss function is converged, obtaining the trained heuristic mobility network, and obtaining diaper wetness of the test sample set

FIG. 1

METHOD FOR DETECTING DIAPER WETNESS BASED ON RADIO SIGNAL TECHNOLOGY

CROSS REFERENCE TO THE RELATED APPLICATIONS

This application is the national phase entry of International Application No. PCT/CN2022/133189, filed on Nov. 21, 2022, which is based upon and claims priority to Chinese Patent Application No. 202210904762.9, filed on Jul. 29, 2022, the entire contents of which are incorporated herein by reference.

TECHNICAL FIELD

The present invention relates to the technical field of intelligent health detection, and in particular to a method for detecting diaper wetness based on a ratio signal technology.

BACKGROUND

The existing diaper wetness detection method comprises: using a visual aid as a wetness indicator, placing a Bluetooth sensor on the diaper; and installing a radio-frequency identification (RFID) tag on the diaper. The above detection solution for diaper wetness is actually an active inspection of the diaper or the installation of a specific sensor on the diaper, which brings a lot of burdens to the user. Therefore, how to detect the diaper wetness without installing any sensor is a problem that is continuously studied by those skilled in the art.

Radio frequency is a non-contact automatic identification technology. Compared with traditional magnetic card and IC card technology, the radio frequency technology has the characteristics of non-contact, high reading speed, no abrasion, and the like. The radio frequency technology performs non-contact bidirectional data transmission between the reader and the radio frequency card to achieve the purpose of target identification and data exchange. Compared with the traditional barcode, magnetic card and IC card, the radio frequency card has the characteristics of non-contact, high reading speed, no environmental influence, long service life, and convenient use, and simultaneously has the anti-collision function and can simultaneously process a plurality of cards.

To achieve a passive, comfortable, ubiquitous, and radio frequency-based diaper wetness detection solution, several problems are faced: 1. how to extract a representation of a wet diaper from a radio frequency signal, 2. how to eliminate external mobile and static interferences, and 3. how to adapt the solution to a newcomer in a new family; and the above problems are technical problems to be solved urgently by those skilled in the art.

SUMMARY

In view of this, the present invention provides a method for detecting diaper wetness based on a radio signal technology, which can effectively extract a representation of a wet diaper from a radio frequency signal, eliminate external mobile and static interferences, train an excellent model to detect diaper wetness through a heuristic mobility network, and can be well adapted to a newcomer in a new family.

In order to achieve the above objective, the present invention provides the following technical solutions.

A method for detecting diaper wetness based on a ratio signal technology comprises the following steps:

sending a frequency-modulated continuous wave signal to a diaper through a radar device to obtain a transmission signal $S_T(t)$ and a return signal $S_R(t)$ of the radar device;

detecting a static environment factor and a dynamic environment factor based on the transmission signal $S_T(t)$ and the return signal $S_R(t)$, and obtaining continuous radar snapshots;

eliminating interference of the static environment factor and the dynamic environment factor by using a filtering template based on the continuous radar snapshot and object respiration;

obtaining an outline of the diaper by using wavelet synchronous compression transformation, and dividing into a training sample set and a testing sample set; and inputting the training sample set and the test sample set into a heuristic mobility network for training until a loss function is converged, obtaining the trained heuristic mobility network, and obtaining diaper wetness of the test sample set.

Optionally, expressions of the transmission signal $S_T(t)$ and the return signal $S_R(t)$ of the radar device are as follows:

$$S_T(t) = \cos\left(\int_0^t f(t')dt'\right) = \cos\left(2\pi\left(f_c t + \frac{B_s t^2}{2T_s}\right)\right);$$

$$S_R(t) = S_T(t - \tau) = \cos\left(2\pi\left(f_c(t - \tau) + \frac{B_s(t - \tau)^2}{2T_s}\right)\right);$$

wherein $f_c$ is a start frequency, $B_s$ represents a scanning bandwidth, $T_s$ represents scanning time, $\tau$ represents reflection delay of the transmission signal, and attenuation of an amplitude is ignored.

Optionally, the obtaining continuous radar snapshots comprises the following steps:

multiplying the transmission signal $S_T(t)$ and the return signal $S_R(t)$, and filtering apart with the highest frequency to obtain a signal $S_{M1}(t)$;

$$S_{M1}(t) = \cos\left(2\pi\left(f_c\tau - \frac{B_s(\tau^2 - 2t\tau)}{2T_s}\right)\right);$$

detecting the static environment factor through range-fast Fourier transform to obtain a signal $S_{M2}(t)$, $$S_{M2}(t) = rangeFFT(S_{M1}(t));$$

detecting the static environment factor and the dynamic environment factor through Doppler-fast Fourier transform to obtain continuous radar snapshots CRS(t);

$$CRS(t) = dopplerFFT(S_{M2}(t_1, t_2, \ldots, t_{64}));$$

wherein $S_{M2}(t_1, t_2, \ldots, t_{64})$ represents a time sequence of $S_{M2}$.

Optionally, the eliminating interference of the static environment factor and the dynamic environment factor is specifically as follows:

due to multipath interference that is complex and difficult to model, using a background noise elimination method, and filtering multipath interference by collecting dot products of a $CRS_0$ filtering template on an empty bed and signals of the continuous radar snapshots:

$$CRS' = CRS * CRS_0;$$

due to the fact that the diaper is always worn and the individual's breath is also included in the CRS, filtering noise and interference of the static environment and dynamic environment factors by collecting dot products of a $CRS_b$ filtering template in which a user lies on a bed without wearing a diaper and signals of the continuous radar snapshots:

$$CRS'' = CRS' * CRS_b;$$

wherein $CRS_0$ is CRS of an empty bed, and $CRS_b$ is CRS in which the user lies on the bed without wearing the diaper.

Optionally, the obtaining an outline of the diaper comprises the following steps:

eliminating smearing on a time-frequency diagram of the diaper by using wavelet synchronous compression transformation to obtain a first representation of the outline of the diaper;

$$Wsst_f(w_b, \tau) = (\Delta w)^{-1} \sum_{a_k:A} W_f(a_k, \tau) a_k^{-\frac{3}{2}} (\Delta a)_k;$$

wherein $w_b$ is a central value of $$\left[ w_b - \frac{1}{2}\Delta w, w_b + \frac{1}{2}\Delta w \right], \tau$$

represents a resolution time domain, $\Delta w = w_b - w_{b-1}$, $a_k$ represents a discrete value of the scale, and A represents $$|w(a_k, \tau) - w_b| \le \frac{\Delta w}{2}; \quad W_f = a_k^{-\frac{1}{2}} \int_R f(t) \psi\left(\frac{t-\tau}{a_k}\right) dt,$$

f(t) represents a signal corresponding to the wet diaper, $\psi()$ represents a wavelet basis function, $(\Delta a)_k = a_k - a_{k-1}$;

refining a time-frequency representation through a plurality of wavelet synchronous compression transformations to obtain a second representation of the diaper outline;

$$Wsst^{[M]}(w_l, \tau) = \int_{-\infty}^{+\infty} Wsst_f(w_b, \tau)\delta\big(w_l - \tilde{w}_b^{[M]}(w_b, \tau)\big) dw_b;$$

wherein $w_l$ represents an instantaneous frequency, $\delta()$ represents the Kronecker Dirac function, and $$\tilde{w}_b^{[M]}(w_b, \tau)$$

represents instantaneous frequency estimation of $Wsst^{[M]}$ section;

limiting a value of M by the following constraint conditions;

$$\int_{-\infty}^{+\infty} \int_{-\infty}^{+\infty} \big| \tilde{w}_b^{[M]}(w_b, \tau) - \tilde{w}_b^{[M-1]}(w_b, \tau) \big| d\tau dw_b < \varepsilon;$$

wherein $\varepsilon$ is a very small threshold set to 1e-8.

Optionally, the obtaining the trained heuristic mobility network comprises the following steps:

inputting the training sample set and the test sample set into a heuristic mobility network for training;

extracting feature representation by using a Resnet network;

representing a migration difference between the training sample set and the testing sample set through the heuristic mobility network, eliminating the migration difference by using a generative adversarial network mechanism until a loss function of the heuristic mobility network is converged to obtain the trained heuristic mobility network, and obtaining diaper wetness of the testing sample set in feature presentation;

wherein the loss function L(Ttm) of the heuristic mobility network is:

$$L(Ttm) = L_{Rem} + L_{Pro};$$

$$L_{Rem} = E_{x_i^n \sim D_N} \log D(F_i) + E_{x_j^q \sim D_A} \log[1 - D(F_i)];$$

$$L_{Pro} = L_{CrossEntropy}(F_i - H(x_i), y_i);$$

wherein $L_{Rem}$ represents a loss function to eliminate the migration difference, $L_{Pro}$ represents a loss function to predict diaper wetness; $F_i$ represents the extracted features, $H(x_i)$ represents the migration difference, $$E_{x_i^n \sim D_N}$$

represents expectation of a source domain, $D(F_i)$ represents distribution of the extracted features, $$E_{x_j^q \sim D_A}$$

represents expectation of a target domain, $L_{CrossEntropy}$ represents calculating cross entropy of two variables, $y_i$ represents sample labels, $$x_i^n$$

represents a signal from the source domain, $D_N$ represents a source domain set, $$x_j^a$$

represents a signal from the target domain, and $D_A$ represents a target domain set.

It can be seen from the above technical solutions, compared with the prior art, the present invention discloses and provides a method for detecting diaper wetness based on a ratio signal technology, and the method has the following beneficial effects: the present invention detects diapers through frequency-modulated continuous wave (FMCW) signals, senses static environment information and dynamic environment information in a radar field of view (FOV) by using the continuous radio snapshot (CRS) extracted from reflected radio signals, eliminates irrelevant static reflection and irrelevant mobile reflection through a filtering template based on CRS and object respiration, and extracts an outline of the diaper through wavelet synchronous compression transformation; and the technical solutions of the present invention can effectively extract a representation of a wet diaper from radio frequency signals, and eliminate external mobile and static interference; and meanwhile a heuristic mobility network can well solve the problem of adapting to a newcomer in a new family.

BRIEF DESCRIPTION OF THE DRAWINGS

In order to more clearly illustrate the technical solutions in the embodiments of the present invention or in the prior art, the drawings required to be used in the description of the embodiments or the prior art are briefly introduced below. It is obvious that the drawings in the description below are merely embodiments of the present invention, and those of ordinary skill in the art can obtain other drawings according to the drawings provided without creative efforts.

FIG. 1 is a schematic flow chart of a method for detecting diaper wetness according to the present invention;

DETAILED DESCRIPTION OF THE EMBODIMENTS

Figure 2:
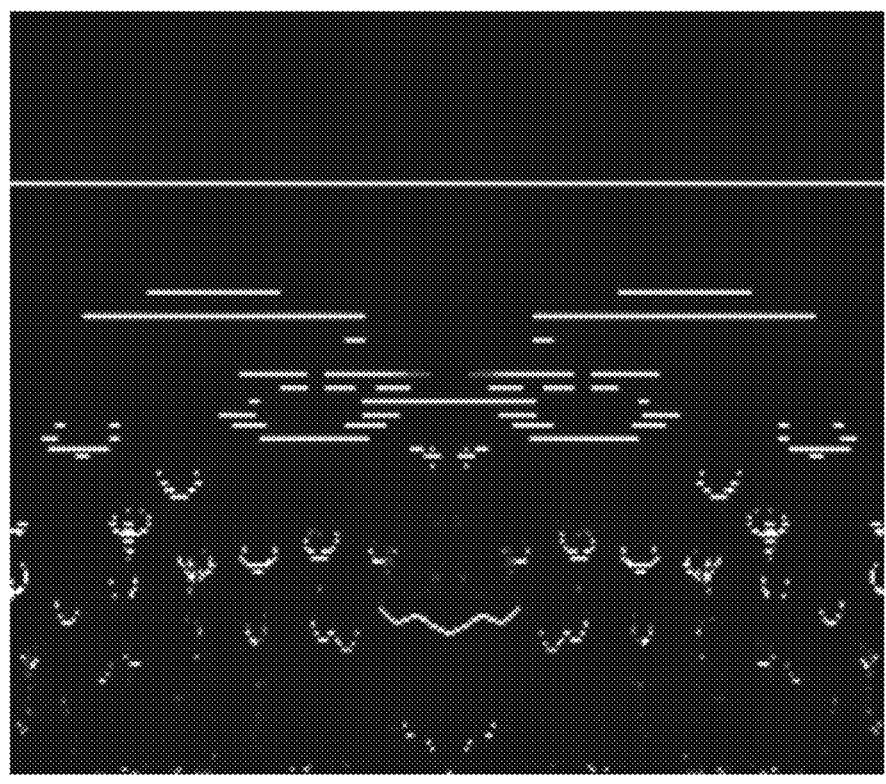
FIG. 2 is a continuous radio snapshot of a dry diaper.

The following clearly and completely describes the technical solutions in embodiments of the present invention with reference to the accompanying drawings in embodiments of the present invention. It is clear that the described embodiments are merely a part rather than all of embodiments of the present invention. Based on the embodiments of the present invention, all other embodiments obtained by those of ordinary skill in the art without creative efforts shall fall within the protection scope of the present invention.

First, by studying the feasibility of radio signals to capture the wetness of a diaper on a subject, it is found that the diaper outline extracted from the radio signals presented a unique pattern for different wet diapers. Base on this, an embodiment of the present invention provides a method for detecting diaper wetness based on a ratio signal technology, as shown in FIG. 1, which comprises the following steps:

sending a frequency-modulated continuous wave signal to a diaper through a radar device to obtain a transmission signal $S_T(t)$ and a return signal $S_R(t)$ of the radar device;

detecting a static environment factor and a dynamic environment factor based on the transmission signal $S_T(t)$ and the return signal $S_R(t)$, and obtaining continuous radar snapshots;

eliminating interference of the static environment factor and the dynamic environment factor by using a filtering template based on the continuous radar snapshot and object respiration;

obtaining an outline of the diaper by using wavelet synchronous compression transformation, and dividing into a training sample set and a testing sample set; and inputting the training sample set and the test sample set into a heuristic mobility network for training until a loss function is converged, obtaining the trained heuristic mobility network, and obtaining diaper wetness of the test sample set.

The solution proposed in this embodiment is passive, ubiquitous, comfortable, non-contact, and non-invasive, does not require the installation of sensors or tags on the surface or inside of the diaper, and can use radio signals to extract unique outline patterns of different diapers to detect wetness of the diaper worn by the subject, even if the environment surrounding the diaper is dark.

The specific solution is as follows:

sending a frequency-modulated continuous wave signal to a diaper to obtain a transmission signal $S_T(t)$ and a return signal $S_R(t)$ of the radar device, wherein expressions of the signals are as follows:

$$S_T(t) = \cos\left(\int_0^t f(t')dt\right) = \cos\left(2\pi\left(f_c t + \frac{B_s t^2}{2T_s}\right)\right);$$

$$S_R(t) = S_T(t-\tau) = \cos\left(2\pi\left(f_c(t-\tau) + \frac{B_s(t-\tau)^2}{2T_s}\right)\right);$$

wherein $f_c$ is a start frequency, $B_s$ represents a scanning bandwidth, $T_s$ represents scanning time, $\tau$ represents reflection delay of the transmission signal, and attenuation of an amplitude is ignored.

Further, the obtaining continuous radar snapshots comprises the following steps:

multiplying the transmission signal $S_T(t)$ and the return signal $S_R(t)$, and filtering apart with the highest frequency to obtain a signal $S_{M1}(t)$;

$$S_{M1}(t) = \cos\left(2\pi\left(f_c\tau - \frac{B_s(\tau^2 - 2t\tau)}{2T_s}\right)\right);$$

detecting the static environment factor through range-fast Fourier transform (range-FFT) to obtain a signal $S_{M2}(t)$;

$$S_{M2}(t) = rangeFFT(S_{M1}(t));$$

detecting the static environment factor and the dynamic environment factor through Doppler-fast Fourier transform (Doppler-FFT) to obtain continuous radar snapshots CRS(t);

$$CRS(t) = dopplerFFT(S_{M2}(t_1, t_2, \ldots , t_{64}));$$

wherein $S_{M2}(t_1, t_2, \ldots , t_{64})$ represents a time sequence of $S_{M2}$.

Further, the eliminating interference of the static environment factor and the dynamic environment factor is specifically as follows:

due to multipath interference that is complex and difficult to model, in this embodiment, using a background noise elimination method, and filtering multipath interference by collecting dot products of a $CRS_0$ filtering template on an empty bed and signals of the continuous radar snapshots:

$$CRS' = CRS * CRS_0;$$

due to the fact that the diaper is always worn and the individual's breath is also included in the CRS, filtering noise and interference of the static environment and dynamic environment factors by collecting dot products of a $CRS_b$ filtering template in which a user lies on a bed without wearing a diaper and signals of the continuous radar snapshots:

$$CRS'' = CRS' * CRS_b;$$

wherein $CRS_0$ is CRS of an empty bed, and $CRS_b$ is CRS in which the user lies on the bed without wearing the diaper.

Figure 3:
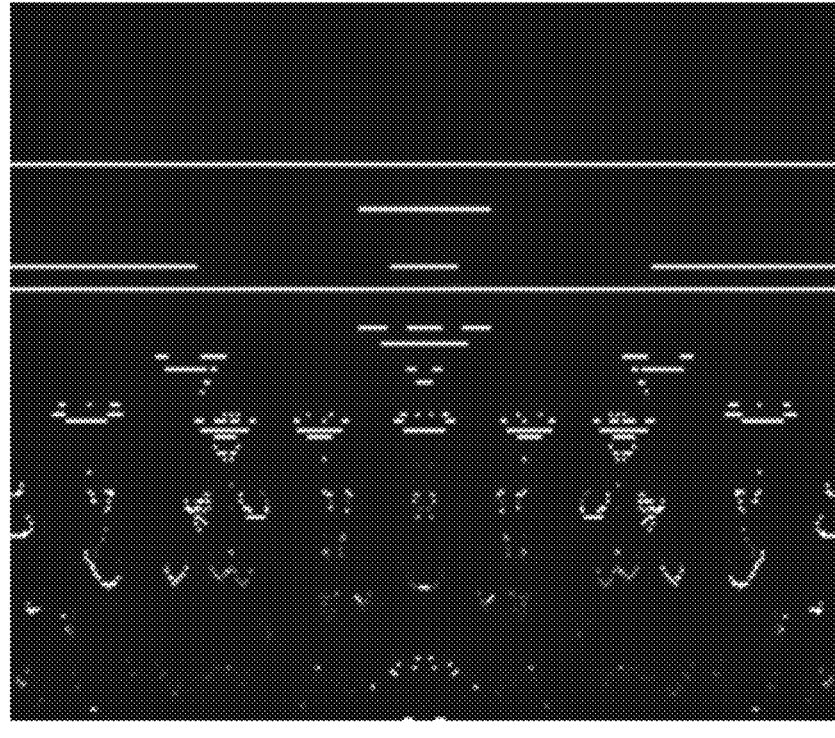
FIG. 3 is a continuous radio snapshot of a wet diaper.

Further, the obtaining an outline of the diaper (referring to FIG. 2 and FIG. 3) comprises the following steps:

eliminating smearing on a time-frequency diagram of the diaper by using wavelet synchronous compression transformation to obtain a first representation of the outline of the diaper;

$$Wsst_f(w_b, \tau) = (\Delta w)^{-1} \sum_{a_k : A} W_f(a_k, \tau) a_k^{-\frac{3}{2}} (\Delta a)_k;$$

wherein $w_b$ is a central value of $$\left[ w_b - \frac{1}{2}\Delta w, w_b + \frac{1}{2}\Delta w \right],$$

$\tau$ represents a resolution time domain, $\Delta w = w_b - w_{b-1}$, $a_k$ represents a discrete value of the scale, and A represents $$|w(a_k, \tau) - w_b| \le \frac{\Delta w}{2}; W_f = a_k^{-\frac{1}{2}} \int_R f(t)\psi\left(\frac{t-\tau}{a_k}\right)dt,$$

f(t) represents a signal corresponding to the wet diaper, $\psi(\ )$ represents a wavelet basis function, $(\Delta a)_k = a_k - a_{k-1}$;

refining a time-frequency representation through a plurality of wavelet synchronous compression transformations to obtain a second representation of the diaper outline;

$$Wsst^{[M]}(w_l, \tau) = \int_{-\infty}^{+\infty} Wsst_f(w_b, \tau)\delta(w_l - \tilde{w}_b^{[M]}(w_b, \tau))dw_b;$$

wherein $w_l$ represents an instantaneous frequency, $\delta(\ )$ represents the Kronecker Dirac function, and $$\tilde{w}_b^{[M]}(w_b, \tau)$$

represents instantaneous frequency estimation of $Wsst^{[M]}$ section;

limiting a value of M by the following constraint conditions;

$$\int_{-\infty}^{+\infty} \int_{-\infty}^{+\infty} |\tilde{w}_b^{[M]}(w_b, \tau) - \tilde{w}_b^{[M-1]}(w_b, \tau)| d\tau dw_b < \varepsilon;$$

wherein $\varepsilon$ is a very small threshold set to 1e-8.

Figure 4:
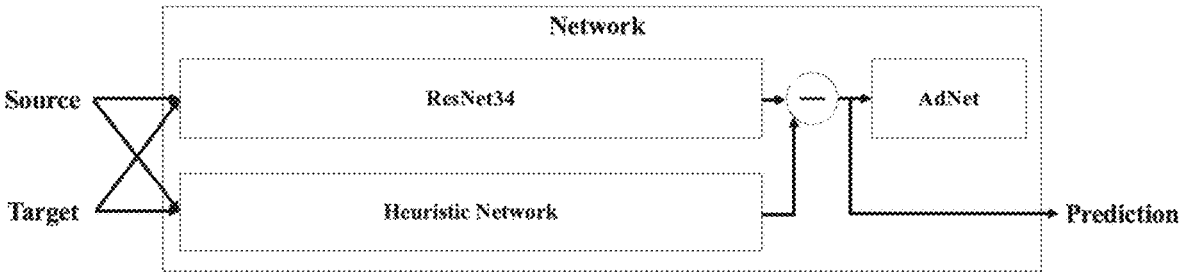
FIG. 4 is a network structure diagram of a heuristic mobility network.

Further, the obtaining the trained heuristic mobility network comprises the following steps:

inputting the training sample set and the test sample set into a heuristic mobility network (referring to FIG. 4) for training;

extracting feature representation by using a Resnet network;

representing a migration difference between the training sample set and the testing sample set through the heuristic mobility network, eliminating the migration difference by using a generative adversarial network mechanism until a loss function of the heuristic mobility network is converged to obtain the trained heuristic mobility network, and obtaining diaper wetness of the testing sample set in feature presentation;

wherein the loss function L(Ttm) of the heuristic mobility network is:

$$L(Ttm) = L_{Rem} + L_{Pro};$$

$$L_{Rem} = E_{x_i^n \sim D_N} \log D(F_i) + E_{x_i^q \sim D_A} \log[1 - D(F_i)];$$

$$L_{Pro} = L_{CrossEntropy}(F_i - H(x_i), y_i);$$

wherein $L_{Rem}$ represents a loss function to eliminate the migration difference, $L_{Pro}$ represents a loss function to predict diaper wetness; $F_i$ represents the extracted features, $H(x_i)$ represents the migration difference, $$E_{x_i^n \sim D_N}$$

represents expectation of a source domain, $D(F_i)$ represents distribution of the extracted features, $$E_{x_j^q \sim D_A}$$

represents expectation of a target domain, $L_{CrossEntropy}$ represents calculating cross entropy of two variables, $y_i$ represents sample labels, $$x_i^n$$

represents a signal from the source domain, $D_N$ represents a source domain set, $$x_j^a$$

represents a signal from the target domain, and $D_A$ represents a target domain set.

The traditional diaper wetness detection method brings a great burden to a user, and based on the technical solution of the present invention, the wet diaper representation can be effectively extracted from the radio frequency signals, the external static interference and dynamic interference are eliminated, the problem of detecting the diaper wetness under different scenes, distances, directions and other conditions by using radio signals is solved through a heuristic mobility network training model, and the detection of the diaper wetness is completed on the premise of not installing a sensor.

The above description of the disclosed embodiments enables those skilled in the art to implement or use the present invention. Various modifications to these embodiments will be readily apparent to those skilled in the art, and the generic principles defined herein may be applied to other embodiments without departing from the spirit or scope of the present invention. Thus, the present invention is not intended to be limited to these embodiments shown herein but is to be accorded the broadest scope consistent with the principles and novel features disclosed herein.

What is claimed is:

1. A method for detecting diaper wetness based on a radio signal technology, comprising the following steps:

sending a frequency-modulated continuous wave signal to a diaper through a radar device to obtain a transmission signal $S_T(t)$ and a return signal $S_R(t)$ of the radar device;

detecting a static environment factor and a dynamic environment factor based on the transmission signal $S_T(t)$ and the return signal $S_R(t)$, and obtaining continuous radar snapshots, wherein obtaining the continuous radar snapshots comprises: multiplying the transmission signal $S_T(t)$ and the return signal $S_R(t)$, and filtering a part with the highest frequency to obtain a signal $S_{M1}(t)$; detecting the static environment factor through range-fast Fourier transform to obtain a signal $S_{M2}(t)$, wherein $S_{M2}(t)=rangeFFT(S_{M1}(t))$; and detecting the static environment factor and the dynamic environment factor through Doppler-fast Fourier transform to obtain the continuous radar snapshots CRS(t), wherein $CRS(t)=dopplerFFT(S_{M2}(t_1, t_2, \ldots, t_{64}))$; eliminating interference of the static environment factor and the dynamic environment factor by using a filtering template based on the continuous radar snapshots and an individual's breath to obtain interference-eliminated continuous radar snapshots CRS", wherein eliminating interference comprises: filtering multipath interference by collecting dot products of a $CRS_0$ filtering template on an empty bed and signals of the continuous radar snapshots: $CRS'=CRS*CRS_0$; and filtering noise and interference of the static environment factor and the dynamic environment factor by collecting dot products of a CRS filtering template in which a user lies on a bed without wearing the diaper and signals of the continuous radar snapshots: $CRS''=CRS'*CRS_b$; wherein $CRS_0$ is CRS of the empty bed, and $CRS_b$ is CRS in which the user lies on the bed without wearing the diaper;

obtaining based on the continuous radar snapshots after eliminating the interference, an outline of the diaper by using wavelet synchronous compression transformation, and dividing the outline of the diaper into a training sample set and a testing sample set; and inputting the training sample set and the testing sample set into a heuristic mobility network for training until a loss function is converged, obtaining a trained heuristic mobility network, and obtaining diaper wetness of the testing sample set in feature presentation, wherein inputting comprises: extracting feature representation by using a Resnet network; representing a migration difference between the training sample set and the testing sample set through the heuristic mobility network; and eliminating the migration difference by using a generative adversarial network mechanism until the loss function of the heuristic mobility network is converged to obtain the trained heuristic mobility network; wherein the Resnet network is a ResNet34 network, and wherein the generative adversarial network mechanism is implemented by an adversarial network (AdNet) coupled to the extracted feature representation.

2. The method according to claim 1, wherein expressions of the transmission signal $S_T(t)$ and the return signal $S_R(t)$ of the radar device are as follows:

$$S_T(t) = \cos\left(\int_0^t f(t')dt\right) = \cos\left(2\pi\left(f_c t + \frac{B_s t^2}{2T_s}\right)\right);$$

$$S_R(t) = S_T(t - \tau) = \cos\left(2\pi\left(f_c(t - \tau) + \frac{B_s(t - \tau)^2}{2T_s}\right)\right);$$

wherein $f_c$ is a start frequency, $B_s$ represents a scanning bandwidth, $T_s$ represents scanning time, $\tau$ represents reflection delay of the transmission signal, and attenuation of an amplitude is ignored.

3. The method according to claim 2, $S_T(t)$ $S_R(t)$ $S_{M1}(t)$ $$S_{M1}(t) = \cos\left(2\pi\left(f_c\tau - \frac{B_s(\tau^2 - 2t\tau)}{2T_s}\right)\right)$$

$S_{M2}(t)$ $$S_{M2}(t) = rangeFFT(S_{M1}(t))$$

CRS(t)

$$CRS(t) = dopplerFFT(S_{M2}(t_1, t_2, \ldots, t_{64}))$$

wherein $S_{M2}(t_1, t_2, \ldots, t_{64})$ represents a time sequence of $S_{M2}$.

4. The method according to claim 1, wherein the step of obtaining the outline of the diaper comprises the following steps:

eliminating smearing on a time-frequency diagram of the diaper by using the wavelet synchronous compression transformation to obtain a first representation of the outline of the diaper;

$$Wsst_f(w_b, \tau) = (\Delta w)^{-1} \sum_{a_k:A} W_f(a_k, \tau) a_k^{-\frac{3}{2}} (\Delta a)_k;$$

wherein $w_b$ is a central value of $$\left[ w_b - \frac{1}{2}\Delta w, \; w_b + \frac{1}{2}\Delta w \right],$$

$\tau$ represents a resolution time domain, $\Delta w = w_b - w_{b-1}$, $a_k$ represents a discrete value of the scale, and A represents $$|w(a_k, \tau) - w_b| \le \frac{\Delta w}{2}; \; W_f = a_k^{-\frac{1}{2}} \int_R f(r) \psi\left(\frac{t-\tau}{a_k}\right) dt,$$

f (t) represents a signal corresponding to a wet diaper, $\psi(\;)$ represents a wavelet basis function, $(\Delta a)_k = a_k - a_{k-1}$;

refining a time-frequency representation through a plurality of wavelet synchronous compression transformations to obtain a second representation of the outline of the diaper;

$$Wsst^{[M]}(w_l, \tau) = \int_{-\infty}^{+\infty} Wsst_f(w_b, \tau) \delta\left(w_l - \tilde{w}_b^{[M]}(w_b, \tau)\right) dw_b;$$

wherein $w_1$ represents an instantaneous frequency, $\delta(\;)$ represents a Kronecker Dirac function, and $$\tilde{w}_b^{[M]}(w_b, \tau)$$

represents instantaneous frequency estimation of $Wsst^{[M]}$ section;

limiting a value of M by the following constraint conditions;

$$\int_{-\infty}^{+\infty} \int_{-\infty}^{+\infty} \left| \tilde{w}_b^{[M]}(w_b, \tau) - \tilde{w}_b^{[M-1]}(w_b, \tau) \right| d\tau dw_b < \varepsilon;$$

wherein $\varepsilon$ is set to 1e-8.

5. The method according to claim 1, wherein the loss function L(Ttm)—of the heuristic mobility network is:

$$L(Ttm) = L_{Rem} + L_{Pro};$$

where $$L_{Rem} = E_{x_i^n \sim D_N} \; \log \; D(F_i) + E_{x_j^a \sim D_A} \; \log[1 - D(F_i)];$$

$$L_{Pro} = L_{CrossEntropy}(F_i - H(x_i), \; y_i);$$

wherein $L_{Rem}$ represents a loss function to eliminate the migration difference, $L_{Pro}$ represents a loss function to predict diaper wetness; $F_i$ represents extracted features, $H(x_i)$ represents the migration difference, $$E_{x_i^n \sim D_N}$$

represents expectation of a source domain, $D(F_i)$ represents distribution of the extracted features, $$E_{x_j^a \sim D_A}$$

represents expectation of a target domain, $L_{CrossEntropy}$ represents calculating cross entropy of two variables, $y_i$ represents sample labels, $$x_i^n$$

represents a signal from the source domain, $D_N$ represents a source domain set, $$x_j^a$$

represents a signal from the target domain, and $D_A$ represents a target domain set.

* * * * *